United States Patent
Shieh et al.

(10) Patent No.: US 9,121,049 B2
(45) Date of Patent: Sep. 1, 2015

(54) PHARMACEUTICAL COMPOSITION FOR ELEVATING RADIO-SENSITIVITY OF CANCER CELLS, PHARMACEUTICAL COMPOSITION FOR DETECTING CANCER CELLS WITH RADIO-SENSITIVITY, AND DETECTION METHOD THEREOF

(71) Applicants: Dar-Bin Shieh, Tainan (TW); Hai-Wen Chen, Tainan (TW); Chia-Chun Chen, Taipei (TW); Ping-Ching Wu, Tainan (TW)

(72) Inventors: Dar-Bin Shieh, Tainan (TW); Hai-Wen Chen, Tainan (TW); Chia-Chun Chen, Taipei (TW); Ping-Ching Wu, Tainan (TW)

(73) Assignee: NATIONAL CHENG KUNG UNIVERSITY, Tainan (TW)

( * ) Notice: Subject to any disclaimer, the term of this patent is extended or adjusted under 35 U.S.C. 154(b) by 3 days.

(21) Appl. No.: 13/628,306

(22) Filed: Sep. 27, 2012

(65) Prior Publication Data

US 2013/0171258 A1 Jul. 4, 2013

Related U.S. Application Data

(60) Provisional application No. 61/539,622, filed on Sep. 27, 2011.

(51) Int. Cl.
*G01N 33/574* (2006.01)
*C12Q 1/04* (2006.01)

(52) U.S. Cl.
CPC ............... *C12Q 1/04* (2013.01); *G01N 33/574* (2013.01); *G01N 33/57423* (2013.01); *G01N 2800/52* (2013.01)

(58) Field of Classification Search
CPC ... C12Q 1/04; G01N 2800/52; G01N 33/574; G01N 33/57423
See application file for complete search history.

(56) References Cited

PUBLICATIONS

Burgman et al., "Cell lin-dependent differences in uptake and retention of the hypoxia-selective nuclear imaging agent Cu-ATSM", Nuclear Medicine and Biology (2005), vol. 32, Issue 6, pp. 623-630.*
Diagaradjane et al., "Modulation of in Vivo tumor radiation response via gold nanoshell-mediated vascular-focused hyperthermia: characterizing an integrated antihypoxic and localized vascular disrupting targeting strategy" Nano Letters (2008), vol. 8, No. 5, pp. 1492-1500.*
Soon et al., "Diacetylbis(N(4)-methylthiosemicarbazonato) copper(II) (CU(II)(atsm)) protects against peroxynitrite-induced nitrosative damage and prolongs survival in amyotrophic lateral sclerosis mouse model" The Journal of Biological Chemistry, (Dec. 2011), vol. 286, pp. 44035-44044.*
Torres et al., "Synthesis of 65Cu(II)-bis(dithiocarbamatebisphosphonate) and its conjugation with superparamagnetic iron oxide nanoparticles: in Ivivo evaluation as dual-modality PET-MRI agent" Angewandte Chemie International Edition, (May 4, 2011), vol. 50, Issue 24, pp. 5509-5513.*
Sartor, "Epidermal Growth Factor Family Receptors and Inhibitors: Radiation Response Modulators" Seminars in radiation Oncology, (2003), vol. 13, No. 1, pp. 22-30.*
Chou et al., "In Vitro and in Vivo Studies of FePt Nanoparticles for Dual Modal CT/MRI Molecular Imaging", J. Am. Chem. Soc., Jun. 24, 2010, vol. 132, pp. 13270-13278.
Katie A. Wood et al., "[64 Cu diacetyl-bis(N4-methyl-thiosemicarbazone)—a radiotracer for tumor hypoxia", Nuclear Medicine and Biology, vol. 35, 2008, pp. 393-400.
Jean-Leon Lagrance et al., "Tumoral Platinum Concentrations in Patients Treated With Repeated Low-Dose Cisplatin as a Radiosensitizer", Int. J. Cancer, vol. 68, 1996, pp. 452-456.
David M. L. Goodgame et al., "Metal Complexes as Radiosensitizers: Cobalt(II), Copper (II), Rhodium (II) and Platinum (II) Complexes of 3-(1-Imidazoyl) Propionic Acid and Some Nitro-Substituted Derivatives, and the Crystal Structure and Radiosensitizer Activity of [CuL2 (H2O)]2·2H2O, Where LH=3-[1-4-Nitroimidazoyl]Propionic Acid", Polyhedron, vol. 11, No. 19, 1992, pp. 2507-2515.

* cited by examiner

*Primary Examiner* — Abigail Fisher
*Assistant Examiner* — Daniel L Branson
(74) *Attorney, Agent, or Firm* — Bacon & Thomas, PLLC

(57) ABSTRACT

The present invention relates to a pharmaceutical composition for elevating radiation-sensitivity of cancer cells, which comprises: a nanoparticle containing with a first element, which is iron, copper, or the combination thereof; and a pharmaceutically acceptable carrier, wherein the nanoparticle is a metal nanoparticle, an alloy nanoparticle, or a metal nanoparticle with core-shell structure, and the size of the nanoparticle is under a controllable range of 3 nm to 150 nm. In addition, the present invention provides a detection method to detect radiation-sensitivity of the cancer cells through different modalities such as CT or MRI due to its native high CT number and magnetic property. Furthermore, the present invention provides a pharmaceutical composition for elevating radiation-sensitivity of the cancer cells through preferential uptake of the nanoparticle, in order to enhance the radiation-sensitivity of the cancer cells and improve the efficiency of radiation therapy to the cancer cells.

6 Claims, 6 Drawing Sheets

PHARMACEUTICAL COMPOSITION FOR ELEVATING RADIO-SENSITIVITY OF CANCER CELLS, PHARMACEUTICAL COMPOSITION FOR DETECTING CANCER CELLS WITH RADIO-SENSITIVITY, AND DETECTION METHOD THEREOF

FIELD OF INVENTION

The present invention relates to a pharmaceutical composition, particularly to a pharmaceutical composition used for detecting whether a cancer cell is radiation resistant. The pharmaceutical composition of the present invention can also be used for increasing radiation-sensitivity of the cancer cells, in order to enhance efficacy of cancer radiation therapy.

DESCRIPTION OF RELATED ART

Cancer is ranked as one of the top ten causes of death in Taiwan, and by estimation one in every six minutes is diagnosed with cancer. In recent years, efforts have been made in progressing development in anti-cancer medicine. Among the novel anti-cancer medicines, focus has been primarily paid to creating anti-cancer medicines with minor side effects. (Sides effects include: nausea, vomiting, stomatitis, and bone marrow suppression) However, it is not necessarily the case where specific cancer cells can be treated by its conventional treatment method.

Treatment for cancer-diagnosed patients can generally be classified into three categories, covering scopes of surgical removal, radiation therapy, and chemotherapy. In those, radiation therapy refers to conventional electrotherapy, which is a medical treatment method mainly focusing on treating local area of a tumor region by using high energy radiation beam to kill cancer cells. However, although high energy radiation beam is one way of killing anomalous cells, it can also pose as a threat to normal cells at the same time. As a result, although radiation therapy shows promises in exceptional efficacy, impact by its side effects remains a major issue to its practice.

Furthermore, literature references and clinical cases have suggested that not all cancer cells are acceptable to radiation therapy. In addition to other constraints complicated by psychological and physical conditions of the patients, some cancer cells also can show radiation resistance before subject to radiation therapy.

As a result, if radiation therapy is performed on a radiation resistant cancer cell, it would be likely that not only could not the cancer cells be treated, but also that the patient's health could face serious burden. Accordingly, if radiation resistance of cancer cells can be pre-evaluated before radiation therapy begins, and appropriate treatment with respect to specific cancer cell characteristics, probabilities for cancer patients' trial-and-error in medical treatment can be expected to decrease.

SUMMARY OF THE INVENTION

Clinically, because a high percentage of tumors having radiation resistance would show high-level expression of metal ion transporter protein, particularly copper transporter protein, the copper transporter protein would also show pushing platinum-containing matter toward cells other than copper. The current invention uses the principles considered above to provide a pharmaceutical composition and its detecting method to detect the fact whether a cancer cell is radiation resistant or not, so as to use platinum or copper containing nanoparticles to detect, before the cancer cell undergoes radiation therapy, if a cancer cell is radiation resistant, so as to serve as a reference for cancer cell treatment.

Another object of the present invention is to provide a pharmaceutical composition, for the purpose of increasing radiation-sensitivity of cancer cell, and thereby increasing treatment efficacy for cancer cell radiation therapy.

In order to achieve the above object, the present invention provides a pharmaceutical composition for detecting if a cancer cell is radiation resistant, comprising: a nanoparticle containing a first element, wherein the first element is copper, platinum, or the combination thereof; and a medical acceptable carrier. The nanoparticle can be a metal nanoparticle, alloy nanoparticle, or a metal nanoparticle having a core-shell structure, wherein the element making up the shell is copper or platinum. The diameter of the nanoparticle can be 3 nm to 150 nm, preferably 6 nm to 100 nm, and more preferably 12 nm.

The above-mentioned nanoparticle further comprises a second element, wherein the second element is at least one selected from the group consisting of: iron, cobalt, palladium, gold, silver, nickel, gadolinium, and silicon. A preferred second element is at least one selected from the group consisting of: iron, cobalt, gold, silver, gadolinium, and silicon; a more preferred second element is at least one selected from the group consisting of: iron, gold, gadolinium, and silicon.

The subject cancer cells for which the current invention's pharmaceutical composition detects can be solid state cancer cell, and the cancer cell type can be lung cancer, breast cancer, prostate cancer, colorectal cancer, gastric cancer, head and neck cancer, ovarian cancer, testicular cancer, bladder cancer, cervical cancer, osteosarcoma, and neuroblastoma tumor. A preferred selection includes lung cancer, breast cancer, prostate cancer, colorectal cancer, gastric cancer, head and neck cancer, bladder cancer. A more preferred selection is lung cancer.

In the pharmaceutical composition, the medical acceptable carrier is not particularly limited. Preferably, the medical acceptable carrier is at least one selected from the group consisting of: active agent, auxiliary agent, dispersing agent, wetting agent, and suspending agent.

Further, the present invention provides a method for detecting if a cancer cell is radiation resistant, comprising the steps of: (A) separately adding nanoparticle having a first element to a first cancer cell and a second cancer cell, wherein the first element is copper, platinum, or the combination thereof; (B) calculating an uptake amount for the first cancer cell and an uptake amount for the second cancer cell; and (C) comparing the uptake amount for the first cancer cell with the uptake amount for the second cancer cell, when the uptake amount of the first cancer cell is at least 2 fold of the uptake amount of the second cancer cell, a first signal is displayed or sent. Following, when the second cancer cell is not resistant to radiation, the first signal would signify that the first cancer cell is radiation resistant.

In the above detection method, because cancer cells would expansively absorb nanoparticles of the present invention due to high-level expression of copper transporter protein, as a result, uptake amount of nanoparticles for cancer cell can be calculated by using inductively coupled plasma atomic emission spectroscopy (ICP-AES), magnetic resonance imaging (MRT), computed tomography (CT), photoacoustic imaging, or near-infrared light in step (B). In addition, in step (C), when the uptake amount of the first cancer cell is 4-10 folds of the uptake amount of the second cancer cell, a second signal is displayed or sent, wherein the second signal signifies that the first cancer cell shows radiation resistance. As a result, the current invention can reuse the above detection method to determine if a cancer cell is resistant to radiation.

In the present invention, if the nanoparticle contains platinum, computed tomography (CT) may be used to detect if cancer cell has the property of radiation resistance. If nanoparticle comprises iron, cobalt, nickel, gadolinium, magnetic resonance imaging (MRI) may be used as the tool of choice for determining if cancer cell is radiation resistant. However, if nanoparticle comprises silicon and infrared laminating material, infrared may be used to detect possibility of radiation resistance in cancer cell.

The nanoparticles used in the above detection methods are metal nanoparticle, alloy nanoparticle, or metal nanoparticle with core-shell structure, wherein the element making up shell is copper or platinum. By way of this the diameter of the nanoparticle can be 3 nm to 150 nm, preferably 6 nm to 100 nm, more preferably 12 nm. Additionally, the nanoparticle further comprises a second element. The second element is at least one selected from the group consisting of: iron, cobalt, palladium, gold, silver, nickel, gadolinium, and silicon group. Preferably, the second element is at least one selected from the group consisting of: iron, cobalt, nickel, gold, silver, gadolinium, and silicon. More preferably, the second element is at least one selected from the group consisting of: iron, cobalt, nickel, gold, gadolinium, and silicon.

As an example, if the nanoparticle of the present invention is an iron-platinum alloy metal nanoparticle, computed tomography (CT) or magnetic resonance imaging (MRI) may be used to detect if cancer cell is radiation resistant. If the nanoparticle of the present invention is a metal nanoparticle with core-shell structure wherein the shell is platinum and core is gold, computed tomography (CT) or photoacoustic imaging may be used to detect if cancer cell is radiation resistant.

Furthermore, the cancer cell detected by the above detection method may be solid state cancer cell, and the types of cancer cell may belong to lung cancer, breast cancer, prostate cancer, colorectal cancer, gastric cancer, head and neck cancer, ovarian cancer, testicular cancer, bladder cancer, cervical cancer, osteosarcoma, and neuroblastoma tumor. Preferably, the cancer cell type belongs to lung cancer, breast cancer, prostate cancer, colorectal cancer, gastric cancer and head and neck cancer. Most preferably, the cancer cell belongs to lung cancer.

Moreover, in order to treat radiation resistant cancer cell, the present invention further proposes a pharmaceutical composition that may increase cancer cell's radiation-sensitivity, comprising: a nanoparticle having a first element, wherein the first element is copper, platinum, or a combination thereof.

Wherein, for another proposed pharmaceutical composition used in increasing radiation-sensitivity of cancer cell, the formation and particle diameter of the nanoparticle, cancer cell kind and type are same as the cancer cell used above for determining radiation resistance.

With respect to radiation resistant cancer cell, ratio of highly expressed copper transporter protein is exceptionally high, and copper transporter protein can transport copper cations, and platinum-containing matter. Therefore, the pharmaceutical composition and detection method of the present invention can utilize the radiation resistance property of cancer cell to first detect radiation resistance property of cancer cell. Before the cancer cell undergoes radiation therapy, the composition and the method of the present invention can also provide a reference for treating cancer cell, by which different treatment approaches may be adopted accordingly based on the possible characteristics of cancer cell in order to obviate undesirable cancer treatment. Additionally, the pharmaceutical composition further provided for increasing radiation-sensitivity of cancer cell can increase radiation-sensitivity of radiation resistant cancer cell, therefore increasing cancer treatment efficacy.

DETAILED DESCRIPTION OF THE PREFERRED EMBODIMENT

Hereafter, examples will be provided to illustrate the embodiments of the present invention. Other advantages and effects of the invention will become more apparent from the disclosure of the present invention. Other various aspects also may be practiced or applied in the invention, and various modifications and variations can be made without departing from the spirit of the invention based on various concepts and applications.

Embodiment 1

Detecting and Screening for Cancer Cells Resistant to Chemical Medicine and Radiation This embodiment uses small cell lung cancer (SCLC) SR3A as cancer cell. First, SR3A cell is screened in vitro for cancer cell line characterized by resistance against radiation; SR3A-13 cell line, and SR3A-14 cell line.

Cancer cells of the present embodiment can be divided into two categories, including experimental group 1, experimental group 2, and a controlled group, wherein experimental group 1 is for SR3A-13 cell line, experimental group 2 is for SR3A-14 cell line, and the control group is for SR3A cell line. Next SR3A-13 cell line of experimental group 1 and SR3A-14 cell line of experimental group 2 are cultured in a Dulbecco's modified eagle medium (DMEM) at 37° C., 5% CO2 or Oswell Park memorial institute medium, wherein the culture medium in DMEM and RPMI has 10% calf serum, and 400 µg/ml of G418 antibiotics. Also, SR3A cell line of controlled group is cultured in culture medium in DMEM and RPMI at 37° C., 5% CO2.

First, the mRNA of hCTR-1 in experimental group 1, experimental 2, and controlled group are detected. The results are shown in FIG. 1. As shown in FIG. 1, the expression amount of mRNA of hCTR-1 of SR3A-13 cell line is 3.29 folds of that for SR3A cell line, the expression amount of mRNA of hCTR-1 cell line is 4.10 fold of that for SR3A cell line.

Then, Western blotting is used to detect protein expression for hCTR-1, for which result is shown in FIG. 2. The result shows expansive expression for hCTR-1 for copper transporter protein in SR3A-13 cell line and SR3-14 cell line. The protein expression amount for SR3A-13 cell line, nCTR-1, is 5.28 fold of that for SR3A; the protein expression amount for SR3A-14 cell line, hCTR-1, is 5.51 fold of that for SR3A. As a result, SR3A-13 cell line and SR3A-14 cell line of the current embodiment both show expansive expression for hCTR-1 for copper transporter protein.

Then, experimental group 1, experimental group 2, and controlled group are subjected to irradiation at 0 Gy, 2 Gy, 4 Gy, 6 Gy, and 8 Gy of radiation dosage, and cell surviving fraction is observed, for which results are shown in FIG. 3. With a radiation dosage of 6 Gy and 8 Gy, experimental group 1 (SR3A-13 cell line) and experimental group 2 (SR3A-14 cell line) show higher cell surviving fraction than controlled group (SR3A cell line). This proves that SR3A-13 cell line and SR3A-14 cell line of the current embodiment have more radiation resistance than SR3A cell line.

It would therefore be understood that the experimental results of the current embodiment that cancer cell having radiation resistance show expansive expression of copper transport protein of hCTR-1.

Embodiment 2

Detecting if Cancer Cell is Radiation Resistant

This embodiment takes pharmaceutical composition made of iron-platinum alloy nanoparticle (FePt) and medical acceptablecarrier as a pharmaceutical composition for detecting if cancer cell is radiation resistant. The pharmaceutical composition can be classified into three groups depending on the particle diameter of iron-platinum alloy nanoparticle, which each is for iron-platinum alloy nanoparticle having a diameter of 3 nm, iron-platinum alloy nanoparticle having a diameter of 6 nm, and iron-platinum alloy nanoparticle having a diameter of 12 nm The preparation method for making iron-platinum alloy nanoparticle having a particle diameter of 3 nm is: in a nitrogen-filled atmosphere, Pt(acac)$_2$(97 mg), 1,2-hexadecane diol (195 mg), and dioctyl ether (10 mL) is mixed, then the mixture solution is heated to result therefrom to 100° C. for 10 minutes. Next, at 100° C., Fe(CO)$_5$ (66 μL), oleylamine (80 μL), and oleic acid (804) is added into the mixture solution, and the mixture solution is heated to 297° C. After the reaction goes on for 30 minutes, the product down is cooled to room temperature, and ethanol is added to precipitate the product, followed by separating the product out by using centrifugation. Furthermore, the reaction solution is heated at a rate of 15° C./min to 240° C. After the reaction proceeds for 30 minutes, the product is cooled down to room temperature, and the product is separated out by using centrifugation. Lastly, the method for making iron-platinum nanoparticle with a particle diameter of 12 nm is: in a nitrogen-filled atmosphere, Pt(acac)$_2$ (195 mg), 1,2-hexadecane idol (1.05 g), dioctyl ether (4 mL), Fe(CO)$_5$ (66 μL), oleylamine (4 mL), and oleic acid is mixed to prepare a reaction solution. Then the reaction solution is heated at a rate of 15° C./min to 240° C., and the reaction solution is kept at 240° C. for 60 minutes. Then, the reaction solution is cooled down to room temperature, ethanol is added to precipitate product, and centrifugation is used to isolate the product.

The culturing condition for the cell line of the present embodiment is the same as in embodiment 1, and is also broken down into Experimental Group 1, Experimental Group 2, and Controlled Group, wherein Experimental Group 1 includes SR3A-13 cell line, Experimental Group 2 includes SR3A-14 cell line, and Controlled Group includes SR3A cell line. Next, three groups of pharmaceutical compositions are added, where each one has a concentration of 1.6 mg/ml separately into the cell lines in Experimental Group 1, Experimental Group 2, and Controlled Group. The pharmaceutical compositions are cultured for 24 hours, and inductively coupled plasma atomic emission spectroscopy (ICP-AES) is used to calculate the uptake amount of iron-platinum alloy nanoparticle for cell line. Result is shown in FIGS. 4 and 5.

FIG. 4 shows the result of the cell line's uptake of 3 nm iron-platinum alloy nanoparticle in embodiment 2, and FIG. 5 shows the result of the cell line's uptake of 6 nm iron-platinum alloy nanoparticle in embodiment 2. As can be seen by the result of FIG. 4, the uptake amount of 3 nm iron-platinum nanoparticle for SR3A-13 cell line and the SR3A-14 cell line is approximately 2 folds of the uptake amount for SR3A cell line. Findings in FIG. 5 suggest that the uptake amount of iron-platinum nanoparticle having 6 nm particle diameter for SR3A-13 cell line is approximately 2.5 folds of the uptake amount for the SR3A cell line, and the uptake amount of iron-platinum alloy nanoparticle having 6 nm particle diameter for SR3A-14 cell line is 3 folds of the uptake amount for SR3A cell line. Also to be noted, the uptake amount of iron-platinum alloy nanoparticle having 12 nm is about 3 folds of the uptake amount for SR3A cell line, and the uptake amount of iron-platinum alloy nanoparticle having particle diameter of 12 nm for SR3A-14 cell line is about 3 folds of the uptake amount for SR3A cell line.

It would be understood by skilled field experts, based from the cited embodiments, that in terms of the uptake amount of iron-platinum alloy nanoparticle, the amount for the radiation resistant SR3A-13 cell line and SR3A-14 cell line are obviously greater (by a magnitude of 2 folds) than that for radiation non-resistant SR3A cell line. This adds weight to strengthen the proposed efficacy enhancement of the invention embodiments: iron-platinum-nanoparticle-containing pharmaceutical composition can be noticeably absorbed by radiation resistant SR3A-13 cell line and SR3A-14 cell line. As such, the pharmaceutical composition containing iron-platinum alloy nanoparticle of the current embodiment can be used in detecting if a cancer cell is radiation resistant. Here, particular mention is made to point out that iron-platinum nanoparticles having particle diameter of 6 nm and 12 nm deliver better results than iron-platinum nanoparticle having 3 nm for particle diameter. Essentially, radiation resistance detection for cancer cell is accomplished by way of examining if cancer cell can absorb pharmaceutical composition containing iron-platinum alloy nanoparticle.

Moreover, the pharmaceutical composition of the present embodiment can be applied with a detector. When the calculation result (through the inductively coupled plasma atomic emission spectroscopy (ICP-AES)) shows that the uptake amounts of iron-platinum alloy nanoparticle for Experimental Group 1, and Experimental Group 2 are greater than at least 2 folds that of Controlled Group, the detector will display a signal to indicate that the cancer cells of Experimental Group 1, and Experimental Group 2 are radiation resistant.

Embodiment 3

Increasing Radiation-Sensitivity of Cancer Cell

The SR3A-13 cell line used in this embodiment is the same as that used in embodiment 1. In this embodiment, experimental group and controlled group are provided, and each contains 5000 SR3A-13 cells. 0.79 mg/ml of 12 nm iron-platinum alloy nanoparticle containing pharmaceutical composition is added to the experimental group's SR3A-13 cell line at 37° C., and cultured for 24 hours. Pharmaceutical composition containing iron-platinum nanoparticle is not added to the controlled group.

Next, after irradiating 6 Gy of radiation dosage of radiation on the experimental group and controlled group, the living status of the cells are observed, and results for which are shown in FIGS. 6A, 6B, and 7. FIG. 6A shows result from after exposure to radiation in the controlled group for embodiment 3 according to the present invention. FIG. 6B shows result from after exposure to radiation in the experimental group for embodiment 3 according to the present invention. FIG. 7 shows result of quantification of increase in cancer cell line radiation-sensitivity for embodiment 3 according to the present invention. It can be seen that with a radiation dosage of 6 Gy and culturing by the pharmaceutical composition having iron-platinum alloy nanoparticle with particle diameter of 12 nm, the cell number in the radiation resistant SR3A-13 cell line is noticeably smaller compared to that in the controlled group.

Furthermore, the cell lines of the Experimental Group 1 of embodiment 1 (SR3A-13 cell line), Experimental Group 2 (SR3A-14 cell line) and Controlled Group (SR3A cell line) are separately added with or without 0.75 mg/ml of pharmaceutical composition containing iron-platinum alloy nanoparticle of 12 nm particle diameter. Then a radiation dosage of 2 Gy, 4 Gy, 6 Gy, 8 Gy is added, at 37° C. for 24 hours of culturing, and the cell surviving fraction is observed. The results are shown in FIG. 8. When pitted under comparison, the surviving fraction of radiation resistant SR3A-13 cell line, SR3A-14 cell line, which are both cultured with pharmaceutical composition having iron-platinum alloy nanoparticle, and both irradiated by radiation dosages of 2 Gy, 4 Gy, 6 Gy, 8Gy, are noticeably lower than those of SR3A-13 cell line, SR3A-14 cell line that are not added with pharmaceutical composition having iron-platinum alloy nanoparticle. The above result is a confirmation that the pharmaceutical composition having iron-platinum nanoparticle of the present embodiment can not only increase radiation-sensitivity of cancer cell, but can also significantly increase radiation-sensitivity of radiation resistant cancer cell.

Considering the above embodiments in sum, the pharmaceutical composition of the current invention has the capability of effectively detecting if a cancer cell is radiation resistant, and the pharmaceutical composition used in increasing radiation-sensitivity of cancer cell can also work to distinctly increase radiation-sensitivity of cancer cell, and thereby shoot up therapeutic efficacy for cancer cell radiation therapy.

The above embodiments are for the purpose of better describing the current invention and are of exemplary nature only, the scope of right asserted by the current invention is based on the scope of claims in this application, and are not intended to be restricted by the above embodiments.

DESCRIPTION FOR LIST OF REFERENCE NUMERALS

None

Figure 1:
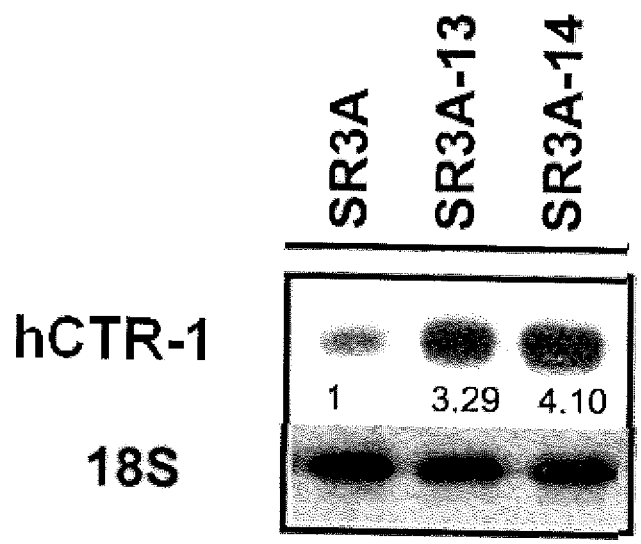
FIG. 1 is a graph showing mRNA expression for hCTR-1 for embodiment 1 according to the present invention.
Figure 2:
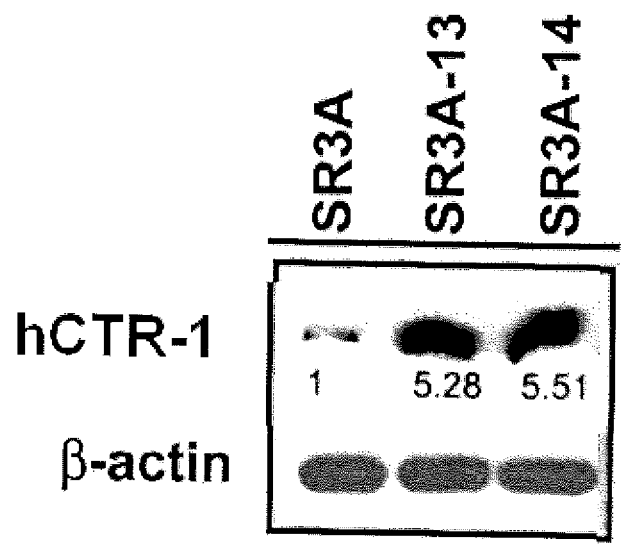
FIG. 2 is a graph for protein expression for embodiment 1 according to the present invention.
Figure 3:
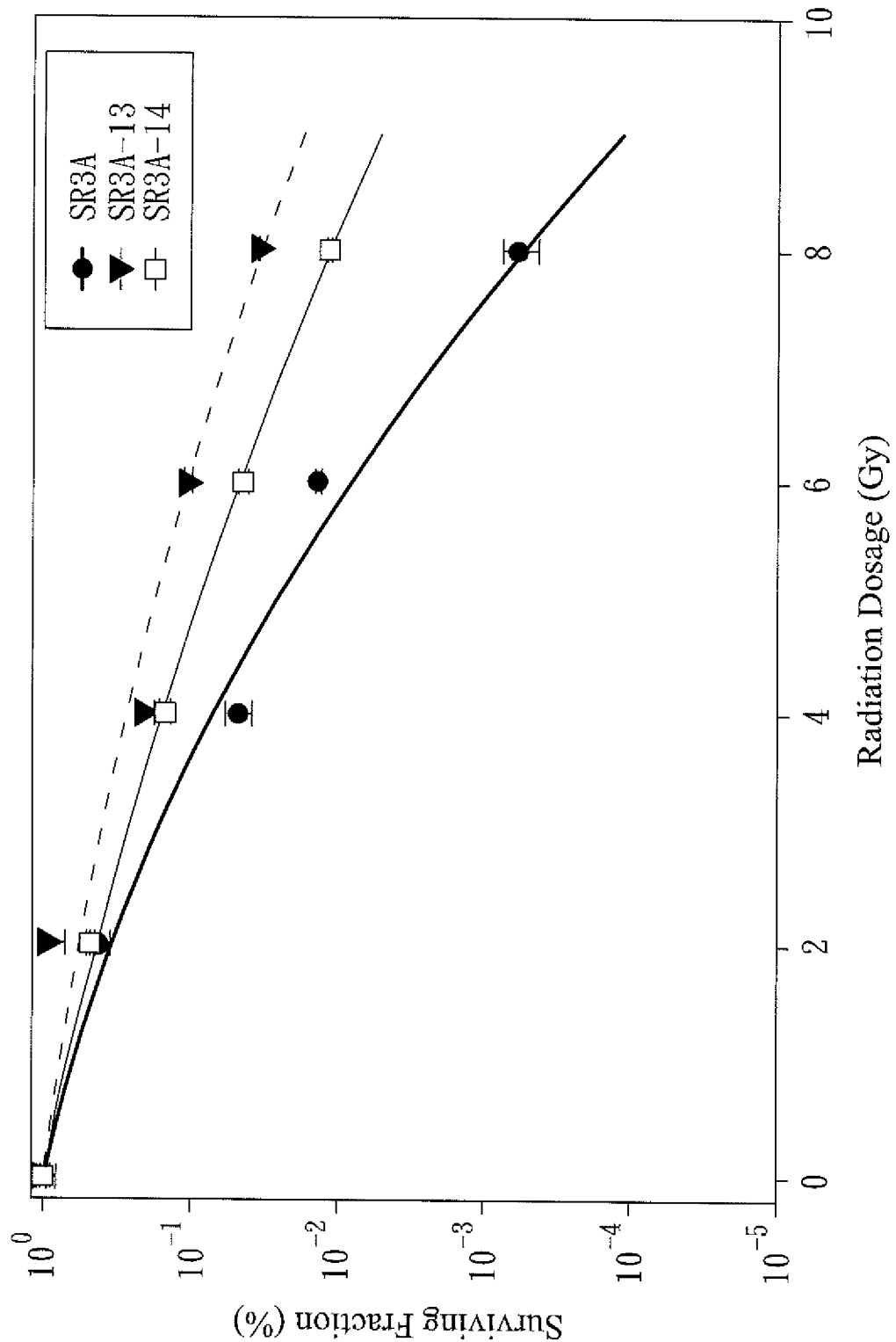
FIG. 3 shows survival result for cell line exposed to radiation for embodiment 1 according to the present invention.
Figure 5:
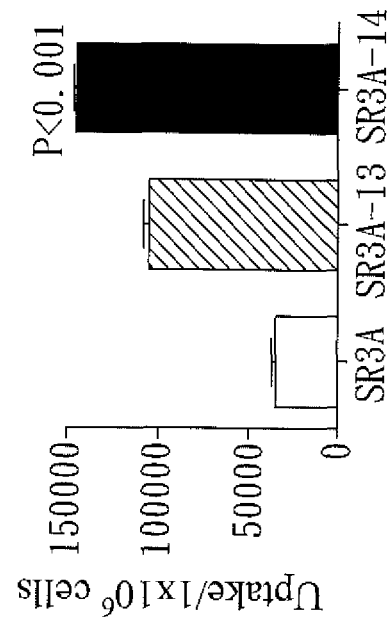
FIG. 5 shows a cell line absorbing 6 nm of iron-platinum alloy nanoparticle for embodiment 2 according to the present invention.
Figure 4:
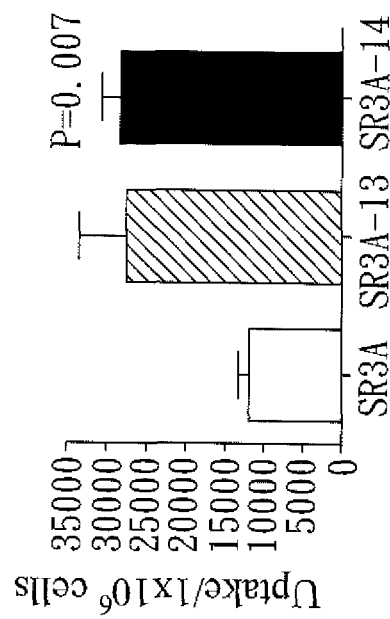
FIG. 4 shows a cell line absorbing 3 nm of iron-platinum alloy nanoparticle for embodiment 2 according to the present invention.
Figure 6A:
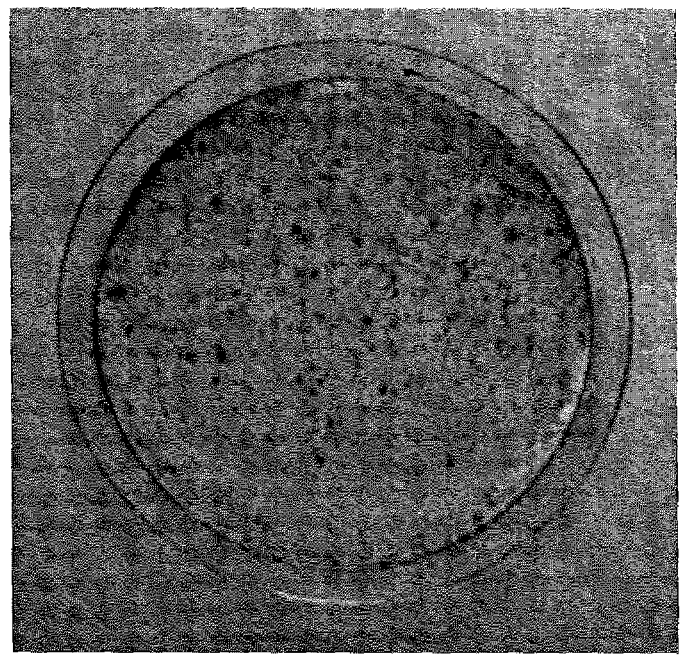
FIG. 6A shows result from after exposure to radiation in the controlled group for embodiment 3 according to the present invention.
Figure 6B:
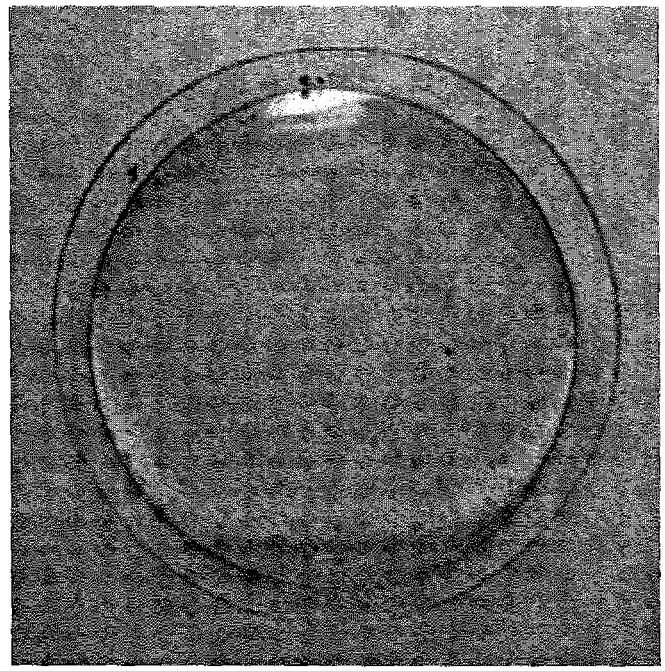
FIG. 6B shows result from after exposure to radiation in the experimental group for embodiment 3 according to the present invention.
Figure 7:
FIG. 7 is a result of quantification of increase in cancer cell line radio-sensitivity for embodiment 3 according to the present invention.
Figure 8:
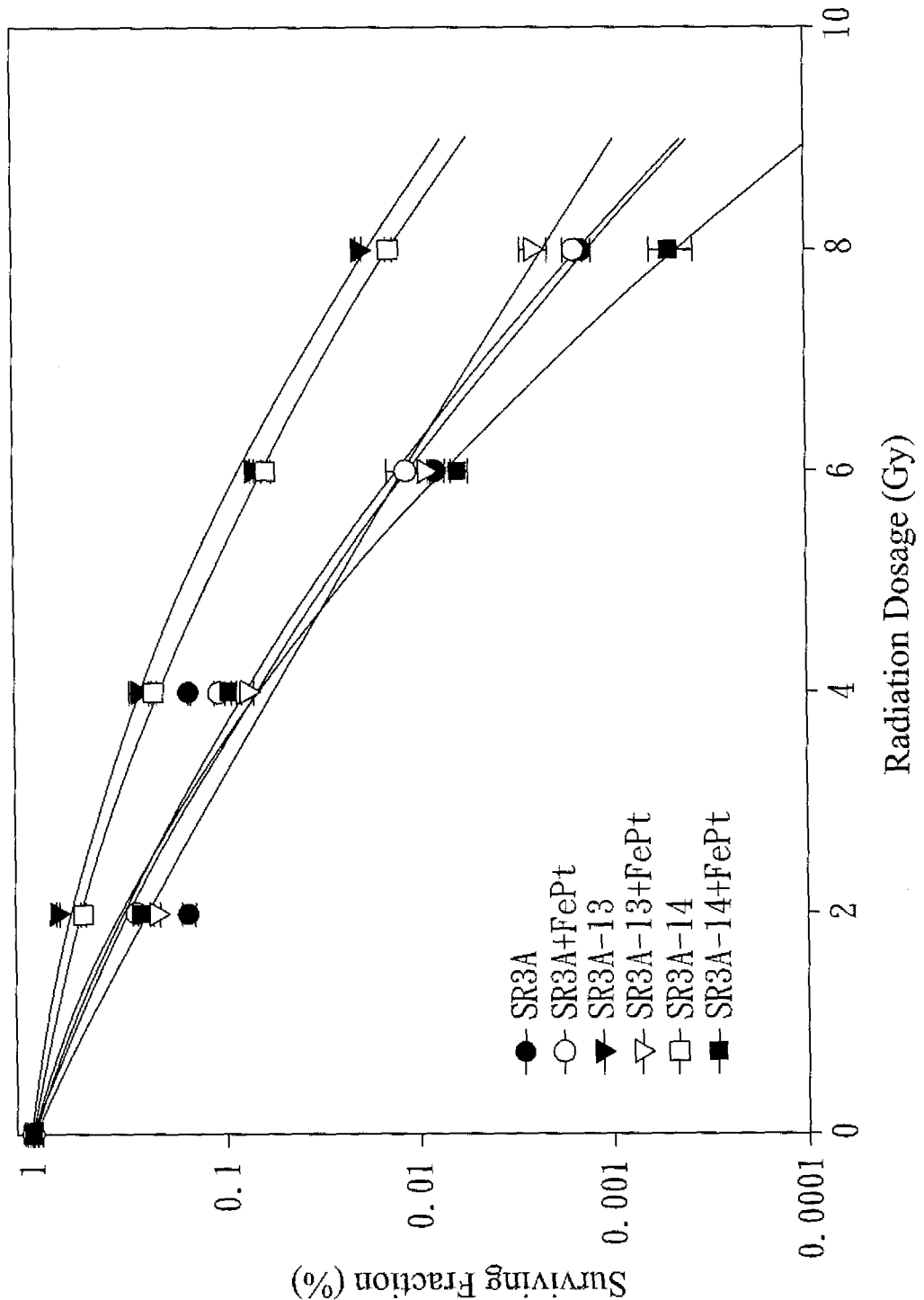
FIG. 8 shows a result of increase in cancer cell line radiation-sensitivity for embodiment 3 according to the present invention.

What is claimed is:

1. A method for detecting if a cancer cell is radiation resistant, comprising the steps of:
   (A) individually adding a nanoparticle consisting essentially of a first element and a second element to a first cancer cell and a second cancer cell, wherein the first element is platinum, the second element is at least one selected from the group consisting of: iron, cobalt, palladium, silver, nickel, and gadolinium, and the diameter of the nanoparticle is 3 nm to 12 nm;
   (B) calculating the uptake amount of the first cancer cell and the uptake amount of the second cancer cell; and
   (C) comparing the uptake amount of nanoparticle for the first cancer cell and for the second cancer cell, and showing or sending a first signal when the uptake amount of the first cancer cell is at least two folds of the uptake amount of the second cancer cell,
   wherein the first signal indicates the first cancer cell is resistant to radiation, and
   wherein the increased uptake amount of the first cancer cell as compared to the second cancer cell is due to copper transporter protein hCTR-1 expression in the first cancer cell.

2. The method according to claim 1, wherein the nanoparticle is a metal nanoparticle, alloy nanoparticle, or metal nanoparticle with a core-shell structure.

3. The method according to claim 1, wherein in step (B), the uptake amount of the nanoparticles for cancer cell is calculated by inductively coupled plasma atomic emission spectroscopy (ICP-AES), magnetic resonance imaging (MRI), computed tomography (CT), photoacoustic imaging, or near-infrared.

4. The method according to claim 1, wherein step (C) further comprises showing or sending a second signal when the uptake amount of the first cancer cell is at least 4-10 folds of the uptake amount of the second cancer cell.

5. The method according to claim 1, wherein the first cancer cell is a solid state cancer cell.

6. The method according to claim 5, wherein the first cancer cell is a lung cancer cell.

* * * * *